United States Patent
Hensel

(12) 
(10) Patent No.: US 6,677,726 B2
(45) Date of Patent: Jan. 13, 2004

(54) SUPPORTING CHARGER FOR RECHARGEABLE APPLIANCES

(75) Inventor: Keith James Hensel, Naremburn (AU)

(73) Assignee: Sunbeam Corporation Limited, Campsie (AU)

( * ) Notice: Subject to any disclaimer, the term of this patent is extended or adjusted under 35 U.S.C. 154(b) by 0 days.

(21) Appl. No.: 10/152,248

(22) Filed: May 20, 2002

(65) Prior Publication Data
US 2003/0098669 A1 May 29, 2003

(30) Foreign Application Priority Data
Nov. 27, 2001 (AU) .............................. PR9135

(51) Int. Cl.[7] .............................................. H01M 10/46
(52) U.S. Cl. ....................................... 320/108; 320/114
(58) Field of Search ................................. 320/107, 108, 320/112, 113, 114, 115

(56) References Cited

U.S. PATENT DOCUMENTS

| 5,075,615 A | * | 12/1991 | Dantis |
| 5,587,645 A | | 12/1996 | Sciammarella et al. |
| 5,736,830 A | * | 4/1998 | Weng |
| 6,040,680 A | * | 3/2000 | Toya et al. |
| 6,181,104 B1 | * | 1/2001 | Rhoads |
| 6,377,022 B1 | * | 4/2002 | Rhoads |
| 6,483,273 B1 | * | 11/2002 | Lee |

FOREIGN PATENT DOCUMENTS

| EP | 1024646 A1 | 8/2000 |
| FR | 2683713 A1 | 5/1993 |
| JP | 09245844 A | 9/1997 |
| JP | 10005045 A | 1/1998 |
| JP | 11056879 A | 3/1999 |
| WO | WO 00/62706 A1 | 10/2000 |

* cited by examiner

Primary Examiner—Edward H. Tso
(74) Attorney, Agent, or Firm—William Michael Hynes; Townsend and Townsend and Crew LLP

(57) ABSTRACT

A rechargeable electric toothbrush 10 is received within a charger 11. The toothbrush 10 includes an outer body 12 that receives a toothbrush assembly 13. Within the body 12, there is located a secondary electric circuit 22 including a secondary coil 23. Upon the secondary coil 23 being energized, DC electric power is delivered to the batteries 21 for charging purposes. The socket 25 includes a primary circuit including a primary coil 31 that upon being energized causes the secondary coil 23 to produce an AC current, subsequently converted into a DC current for the purposes of charging the battery 21.

7 Claims, 4 Drawing Sheets

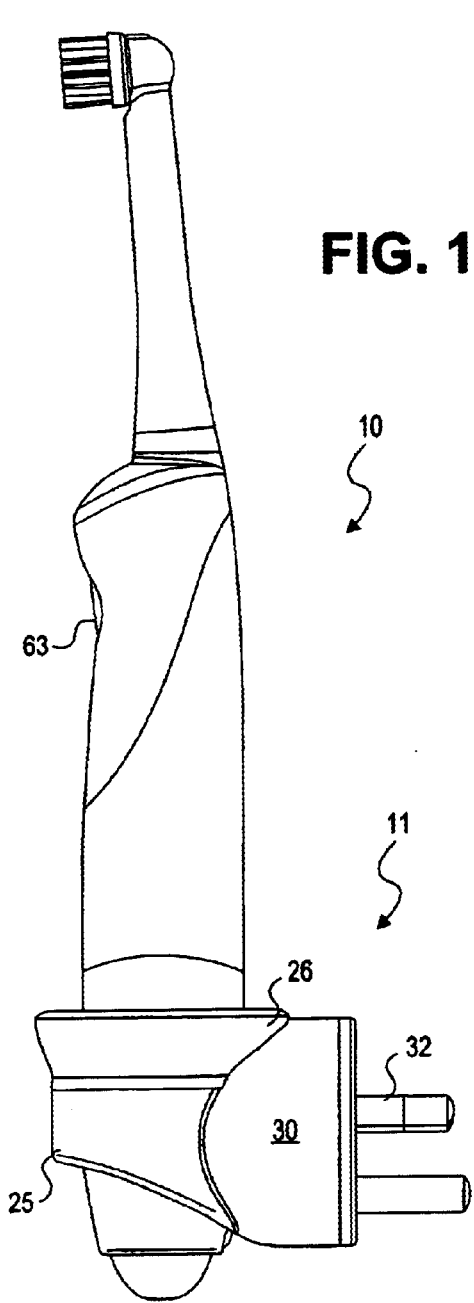
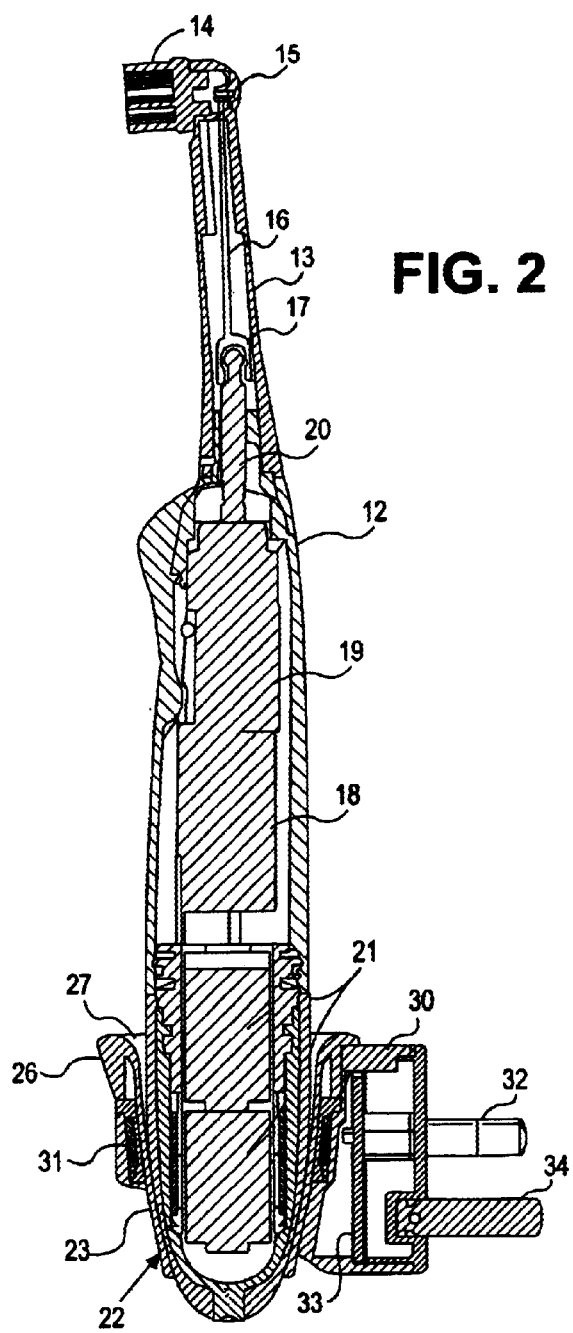

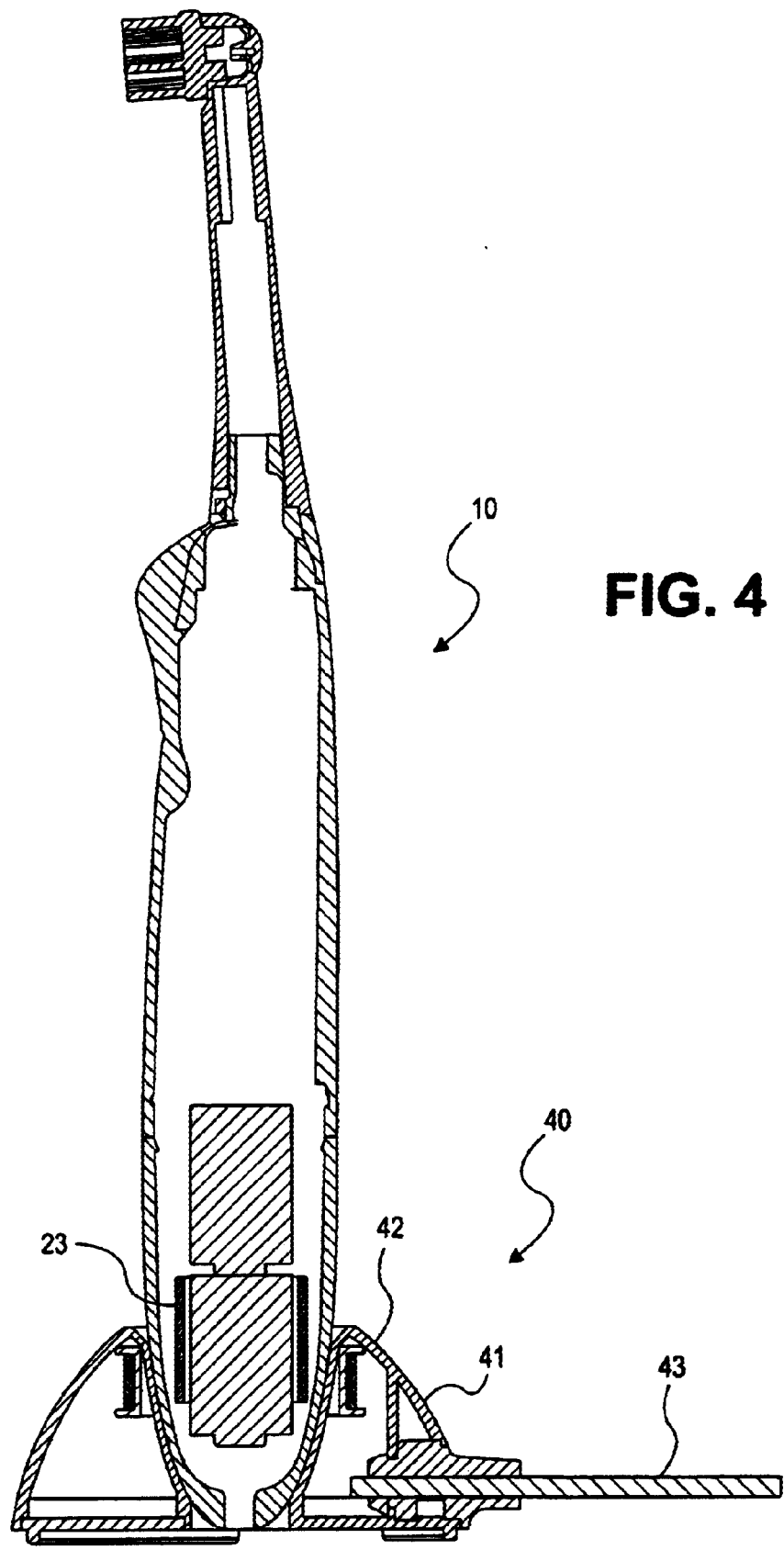

SUPPORTING CHARGER FOR RECHARGEABLE APPLIANCES

TECHNICAL FIELD

The present invention relates to rechargeable appliances and more particularly but not exclusively to an electric tooth brush and charger therefor.

BACKGROUND OF THE INVENTION

Typically, rechargeable tooth brushes are provided with a stand that rests on a bench surface. The stand has a primary coil that interacts with a secondary coil in the tooth brush to charge the batteries within the tooth brush. Extending from the stand is an electric cord terminating with the plug that is engaged within a wall socket to provide the primary coil in the stand with alternating electric power.

The above-described charger for tooth brushes suffers from the disadvantage that the stand occupies bench space and inhibits cleaning of the bench space. This problem is exacerbated by the cord.

Also known are wall-mounted chargers. These have the disadvantage that attachment to a wall is required. They also require a cord.

SUMMARY OF THE INVENTION

It is an object of the present invention to overcome or substantially ameliorate the above disadvantages.

There is disclosed herein a battery charger for an article having a charging secondary circuit including a secondary coil, the charger including:
- a body having a socket with a passage to receive the articles so that the article is supported by the socket with the secondary coil located at least partly in the socket;
- a charging primary circuit in the body and including a primary coil, the primary coil being positioned so as to surround the passage so as to be adjacent the secondary coil when located in the socket;
- at least two connection pins rigidly mounted in the body to engage a wall-mounted AC power supply, the pins being electrically connected to the primary circuit; and wherein:
  - the body and pins are adapted to engage the power supply so that the body is supported thereby together with the article supported in the socket.

Preferably, the socket includes an open top and open bottom to receive the article so that the article is generally vertically oriented.

Preferably, the body further includes a sleeve mounted in the socket, the sleeve having an open top and open bottom to receive the article so that the article is generally vertically oriented.

There is further disclosed herein a combination of the above battery charger and the article, and wherein the article is a rechargeable tooth brush including rechargeable batteries electrically associated with the secondary circuit.

BRIEF DESCRIPTION OF THE DRAWINGS

A preferred form of the present invention will now be described by way of example with reference to the accompanying drawings wherein:

FIG. 1 is a schematic side elevation of a rechargeable tooth brush and charger therefor;

FIG. 2 is a schematic parts section side elevation of the tooth brush and charger of FIG. 1;

FIG. 4 is a schematic section side elevation of the tooth brush of FIG. 1 with an alternative charger;

DESCRIPTION OF THE PREFERRED EMBODIMENTS

Figure 3:
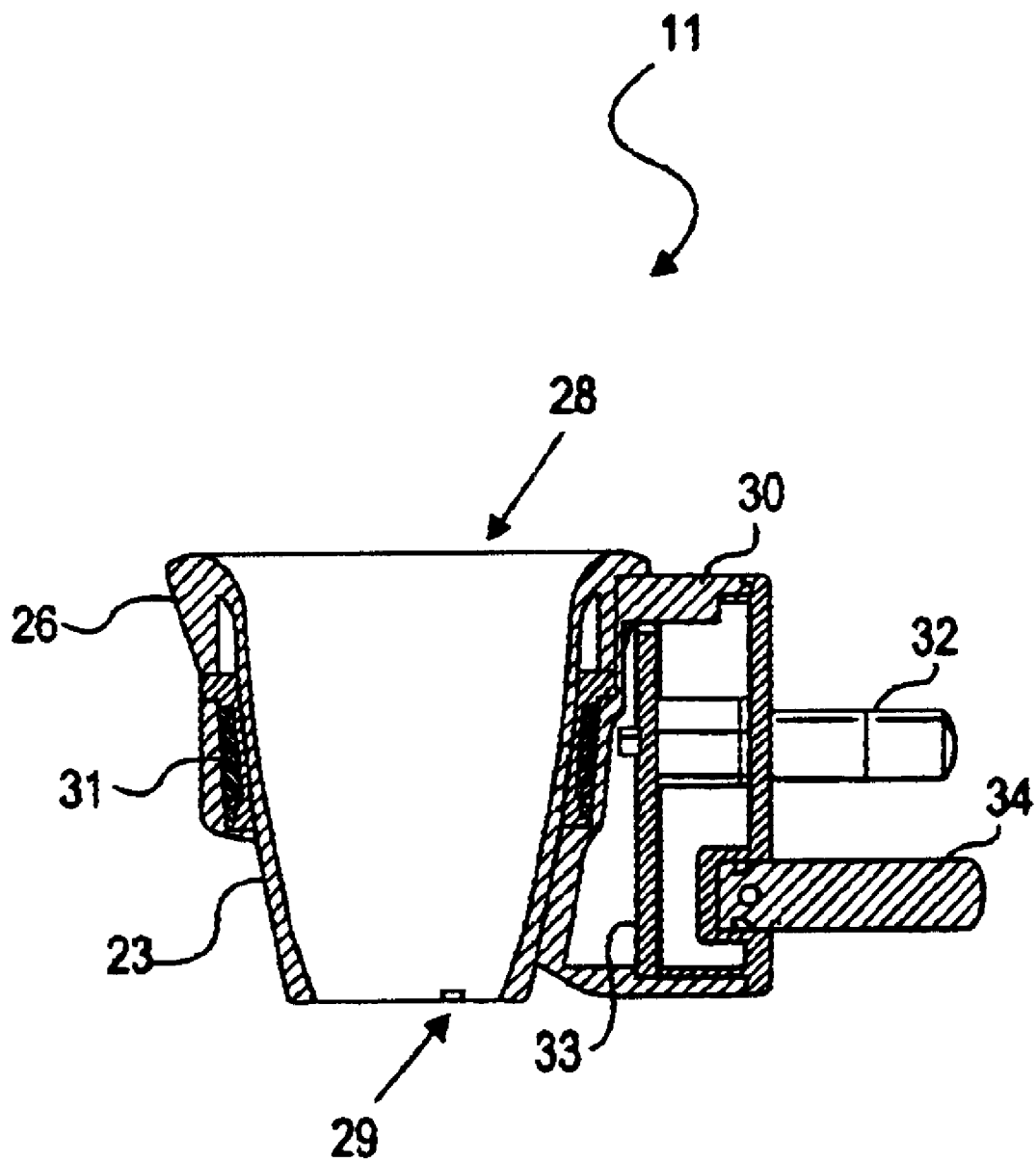
FIG. 3 is a schematic section side elevation of the charger of FIG. 1.

In FIGS. 1 to 3 of the accompanying drawings there is schematically depicted a rechargeable tooth brush 10 that is mounted in a charger 11. The tooth brush 10 includes an outer body 12 that receives a tooth brush assembly 13 terminating with a brush portion 14. Typically, the tooth brush assembly 13 would be detachable from the body 12 so that, upon the brush portion 14 deteriorating, the brush assembly 13 can be replaced.

The brush assembly 13 includes an eccentric crank 15 that is driven by a shaft 16. The shaft 16 is caused to reciprocate to cause angular oscillation of the brush portion 14. The shaft 16 terminates at its lower end with a socket 17.

Located internally of the body 12 is an electric motor 18 that drives a gear assembly 19 that linearly reciprocates a shaft 20, and therefore the shaft 16, to cause angular oscillation of the brush portion 14.

The electric motor 18 is electrically connected to rechargeable batteries 21.

Also located within the body 12 is a secondary electric circuit 22 including a secondary coil 23. Upon the secondary coil 23 being energized DC electric power is delivered to the batteries 21 for charging purposes.

The charger 11 includes a body 24 having a socket 25 with an open top and open bottom through which the lower end of the tooth brush 10 passes. The socket 25 more particularly receives a detachable sleeve 26 that directly receives the tooth brush 10. The sleeve 26 is removable for cleaning purposes and surrounds the lower portion of the tooth brush 10 so that a drainage cavity 27 is provided, tapering toward the lower portion of the sleeve 26. More particularly, the sleeve 26 has an open top 28 and an open bottom 29 through which the tooth brush body 12 projects so as to be generally vertically oriented.

Mounted within the socket 25 is a primary circuit including a primary coil 31 that upon being energized causes the secondary coil 23 to produce an AC current, subsequently converted into a DC current for the purposes of charging the batteries 21.

The body 24 further includes a mounting plug portion 30 having connection pins 32 and 34 that engage a wall-mounted power supply for the purposes of providing alternating electric power for the coil 31. More particularly, the pins 32 are connected to a circuit board 33 which in turn is connected to the primary coil 31.

The pins 32 and 34 are rigidly mounted in portion 30 so that when engaged with the wall-mounted electric supply, the charger 11 is supported thereby. Accordingly, the charger 11 can be maintained in electric contact with the wall-mounted supply with the tooth brush 10 also supported therein.

The above-mentioned tooth brush 10 is also useable with a bench top supported charger 40 shown in FIG. 4. In this instance, the body 41 receives the primary circuit including primary coil 42. The primary circuit receives electric power via a cord 43 extending to a wall-mounted power supply.

It should be noted that the secondary coil 23 extends along the longitudinal axis of the tooth brush 10 so as to have an upper portion and a lower portion, the lower portion being positioned to be associated with the primary coil 42 while the upper portion is to be associated with the primary coil 31. Each coil 31 and 42 is about half the longitudinal length of the coil 23.

Figure 5:
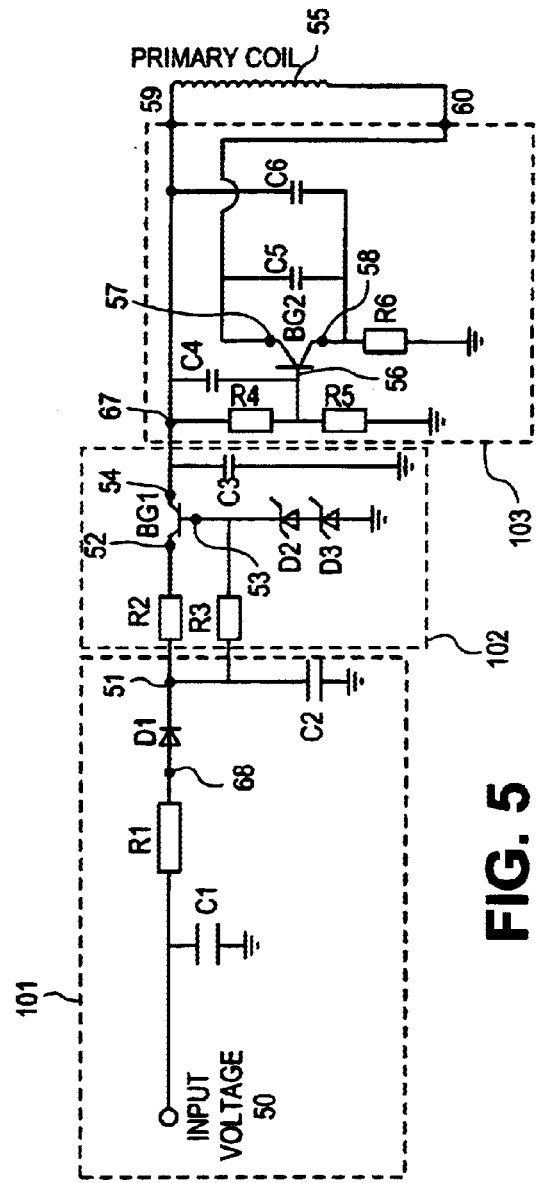
FIG. 5 is a schematic of the primary electric circuit employed in the charger of FIGS. 1 and 4.

FIG. 5 of the accompanying drawings is a schematic of the primary electric circuit employed in the charger 11. The primary electric circuit includes a filter and half wave rectifier circuit 101, a DC voltage regulator circuit 102 and an oscillator circuit 103 feeding a primary coil 55.

The filter-rectifier circuit 101 includes an input voltage terminal 50 connected to one of the pins 32 of FIG. 1 or 4, a capacitor C1 and a resistor R1, where the resistor R1 is connected via junction 68 to the anode of a diode D1 which in turn is connected to a capacitor C2 via junction 51. The capacitors C1 and C2 are connected to neutral via one of pins 32 of FIG. 1 or 4, where capacitor C1 and C2 are chosen to provide filtering. The diode is forward biased at a nominal positive voltage across the diode, where the capacitor C2 attempts to hold the voltage at a constant value, so that the voltage when measured at the junction 51 with respect to neutral is DC with a slight ripple.

The junction 51 forms the input of the voltage regulator circuit 102 which includes resistors R2 and R3, a transistor BG1, zener diodes D2 and D3 and a capacitor C3. Resistors R2 and R3 connect to the output of the filter rectifier circuit 101 via the junction 51. The resistor R2 also connects to the collector 52 of power transistor BG1. The resistor R3 biases the base 53 of power transistor BG1 and the cathode of zener diode D2. The anode of zener diodes D2 connects to the cathode of zener diode D3 and the anode of zener diode D3 is connected to neutral. This configuration maintains a substantially constant voltage at the base 53, and consequently at the emitter 54 of the transistor BG1. The emitter 54 of transistor BG1 is connected to a smoothing capacitor C3.

The voltage output of the DC voltage regulator circuit 102 with respect to neutral can be measured between the emitter 54 of transistor BG1 and neutral to show a nominal DC voltage established by the diodes D2 and D3, with a small ripple arising from the load formed by the oscillator circuit 103.

The oscillator circuit 103 includes resistors R4, R5 and R6, capacitors C4, C5 and C6 and a transistor BG2. The input 67 of the oscillator circuit connects to resistor R4, capacitors C4 and C6 and an output junction 59 of the oscillator circuit 103. The resistor R4 is connected parallel to capacitor C4 via the junction formed at a base 56 of the transistor BG2 and resistor R5. Resistor R5 is connected to a neutral via one of pins 32 of FIGS. 1 and 4. Resistors R4 and R5 are chosen to establish a desired voltage at the base 56 of transistor BG2.

The collector 57 of transistor BG2 connects to capacitor C5 and an output 60 of the oscillator circuit 103. The emitter 58 of transistor BG2 connects to a resistor R6, the capacitor C5, a capacitor C6 and the output terminal 59. The alternate leg of resistor R6 is connected to neutral.

The oscillator circuit 103, when coupled to the primary coil 55, forms an arrangement that oscillates, with the oscillation signal being applied to the primary coil 55. The primary coil 55 may represent either of primary coils 31 or 42 of FIGS. 2 and 4.

Figure 6:
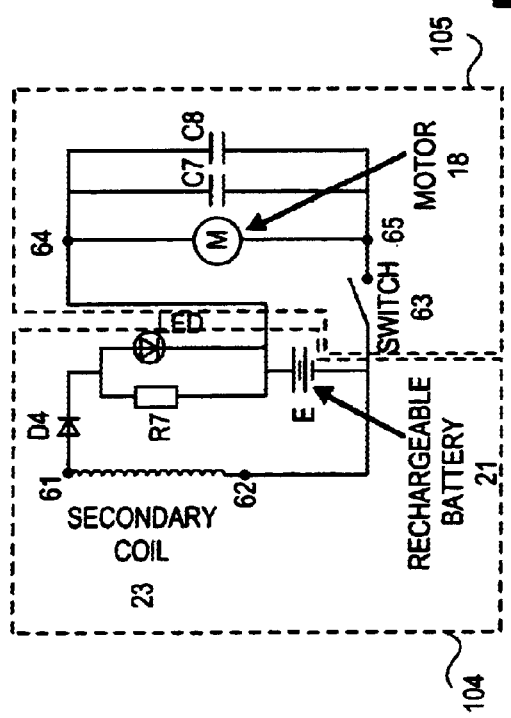
FIG. 6 is a schematic of the secondary electric circuit employed in the toothbrush of FIGS. 1 and 4.

The function of the charger primary electric circuit is to supply an alternating voltage to the primary coil 55. If the toothbrush 10 is mounted into the charger 11 or 40 as shown in FIGS. 1 and 4 and the pins 32 are engaged into a general purpose outlet with 240 V AC power supply applied, the primary coil 55 will have an alternating voltage applied thereto. The alternating voltage across the primary coil 55 will induce an alternating voltage across secondary coil 23 of the secondary electric circuit shown in FIG. 6, when the secondary coil 23 is magnetically coupled to the primary coil 55, for example when the toothbrush is mounted upon the charger.

The secondary electric circuit includes a recharging circuit 104 and a motor circuit 105.

The recharging circuit 104 includes the secondary coil 23, a diode D4, a resistor R7, a Light Emitting Diode (LED) and the rechargeable battery 21. The anode of diode D4 is connected to a terminal 61 of the secondary coil 23 and the cathode of diode D4 is connected to the resistor R7 and the anode of the LED. Resistor R7 and the LED are connected in parallel and to the positive terminal of the rechargeable battery 21. The negative terminal of the rechargeable battery 21 is connected to a terminal 62 of the secondary coil 23. If the voltage induced by the secondary coil at the anode of diode D4 is greater by a nominal value than the voltage E of the rechargeable battery 21, a current will pass into the rechargeable battery 21 via resistor R7 and the LED to recharge the rechargeable battery 21, and also illuminate the LED.

The motor circuit 105 includes an electric motor 18, capacitors C7 and C8 and a switch 63. The positive terminal of the rechargeable battery 21 is connected via the positive terminal 64 of the electric motor 18 as are capacitors C7 and C8. The alternate legs of capacitors C7 and C8 are connected to a negative terminal 65 of the electric motor 18 and the switch 63. The other side of the switch 63 is connected to the negative terminal of the rechargeable battery 21.

When the switch 63 is closed, a differential voltage is applied across the terminals of the electric motor 18 and turns a shaft of the electric motor 18 connected to the gear assembly 19. When the switch 63 is open, there will be no differential voltage applied across the motor and the shaft of the electric motor 18 will not turn.

The foregoing describes a number of embodiments of the present invention, and modifications, obvious to those skilled in the art, can be made thereto without departing from the scope of the invention.

The claims defining the invention are as follows:

1. A battery charger for an article having a charging secondary circuit including a secondary coil, said charger including:
   a body having a socket with a passage to receive said article so that said article is peripherally supported in said socket at said passage with said secondary coil of the article located at least partly in said socket;
   a charging primary circuit in said body and including a primary coil, said primary coil being positioned so as to surround said passage so as to be adjacent to said secondary coil when the article is supported in said socket;
   at least two connection pins rigidly mounted in said body to engage a wall-mounted AC power supply, said pins being electrically connected to said primary circuit; and,
   said body and pins being adapted to engage said power supply so that said body and said article supported in said socket of said body are supported from the wall-mounted AC power supply.

2. The battery charger for an article of claim 1 wherein said socket includes an open top and an open bottom to receive said article so that said article is generally vertically oriented.

3. The battery charger for an article of claim 1 wherein said body further includes a sleeve mounted in said socket, said sleeve having an open top and an open bottom to receive said article so that said article is generally vertically oriented.

4. The battery charger for an article of claim 1 wherein said article is a rechargeable tooth brush including rechargeable batteries electrically associated with said secondary circuit.

5. In combination, a battery charger and an article to be charged thereby:
   said article having an extremity with a charging secondary circuit including a secondary coil located therein;
   said charger including:
      a body having a socket with a passage to receive the extremity of said articles so that said article is supported by said socket with said secondary coil located at least partly in said socket;
      a charging primary circuit in said body and including a primary coil, said primary coil being positioned so as to surround said passage so as to be adjacent said secondary coil when located in said socket;
      at least two connection pins rigidly mounted in said body to engage a wall-mounted AC power supply, said pins being electrically connected to said primary circuit; and wherein:
         said body and pins are adapted to engage said power supply so that said body is supported thereby together with said article supported in said socket.

6. The combination of claim 5 wherein said extremity is a lower extremity and said socket includes an open top and an open bottom to receive said article so that said article is generally vertically oriented with respect to said extremity.

7. The combination of claim 6 where said body further includes a sleeve mounted in said socket, said sleeve having an open top and open bottom to receive said article so that said article is generally vertically oriented.

* * * * *